United States Patent
Belov et al.

(10) Patent No.: US 7,417,228 B2
(45) Date of Patent: Aug. 26, 2008

(54) METHOD OF AND DEVICE FOR DETECTING OIL POLLUTIONS ON WATER SURFACES

(75) Inventors: Michael Leonidovich Belov, Moscow (RU); Victor Aleksandrovich Gorodnichev, Moscow (RU); Valentin Ivanovich Kozintsev, Moscow (RU); Olga Alekseevna Smirnova, Moscow (RU); Yurii Victorovich Fedotov, Moscow (RU); Anastasiva Michailovnan Khroustaleva, Moscow (RU)

(73) Assignee: The United States of America as represented by the United States Department of Energy, Washington, DC (US)

( * ) Notice: Subject to any disclaimer, the term of this patent is extended or adjusted under 35 U.S.C. 154(b) by 9 days.

(21) Appl. No.: 11/554,228

(22) Filed: Oct. 30, 2006

(65) Prior Publication Data

US 2007/0102333 A1    May 10, 2007

(30) Foreign Application Priority Data

Oct. 28, 2005    (RU) ............................... 2005133106

(51) Int. Cl.
  *G01J 1/10*    (2006.01)
(52) U.S. Cl. .................................................. 250/336.1
(58) Field of Classification Search ............... 250/336.1
  See application file for complete search history.

(56) References Cited

U.S. PATENT DOCUMENTS 3,783,284 A * 1/1974 McCormack .......... 250/339.11
5,296,711 A * 3/1994 Leonard et al. ............. 250/372

* cited by examiner

*Primary Examiner*—David Porta
*Assistant Examiner*—Mark R Gaworecki
(74) *Attorney, Agent, or Firm*—Vinit H. Patel; Linda P. Field; Paul A. Gottlieb

(57) ABSTRACT

Detection of oil pollution on water surfaces includes providing echo signals obtained from optical radiation of a clean water area at two wavelengths, optically radiating an investigated water area at two wavelengths and obtaining echo signals from the optical radiation of the investigated water area at the two wavelengths, comparing the echo signals obtained from the radiation of the investigated area at two wavelengths with the echo signals obtained from the radiation of the clean water area, and based on the comparison, determining presence or absence of oil pollution in the investigated water area.

4 Claims, 1 Drawing Sheet

METHOD OF AND DEVICE FOR DETECTING OIL POLLUTIONS ON WATER SURFACES

CROSS-REFERENCE TO A RELATED APPLICATION

The invention described and claimed hereinbelow is also described in Patent Application RF 2005133106 filed on Oct. 28, 2005 in Russian Federation. This Patent Application, whose subject matter is incorporated herein by reference, provides the basis for a claim of priority of invention under 35 U.S.C. 119(a)-(d).

BACKGROUND OF THE INVENTION

The present invention relates to a method of and a device for detecting oil pollutions on water surfaces.

A method of detection of oil film on water surface is known from inventor's certificate of the USSR # 1,354,073. In the method the investigated water surface is illuminated by pulsed optical beam and the reflected signal is received. Comparison of signals from clean and from investigated water areas is conducted. Amount of pulses, which exceeds the threshold of the analyser, is selected as comparison parameter. If $N \geq N_b$ then it is supposed that oil film is present, and if $N < N_b$ then oil film is not present. $N_b$ is a quantity that specifies probability of signal reception in roughness conditions. A disadvantage of this method is low reliability of detection.

Another method of oil pollution detection is disclosed in patent Russian Federation No. 2,143,108. Water surface is irradiated by pulsed optical beam and the reflected signal is received. Comparison of signals from clean and from investigated water areas is conducted. Energy of echo pulses are selected as comparison parameters. It is supposed that oil film is present if both conditions are fulfilled:

$$W > W_0$$

$$\tau < \tau_0$$

where $W_1$ $W_0$ and $\tau < \tau_0$ are energies and widths of echo pulses reflected from investigated and clean water areas correspondingly. A disadvantage of this method is false detection of oil pollution in the presence of areas with smoothed wind roughness on clean water surface.

SUMMARY OF THE INVENTION

It is therefore an object of the present invention to provide a method of and device for detecting oil pollutions on water surfaces which avoid the disadvantages of the prior art.

In keeping with these objects and with others which will become apparent hereinafter, one feature of the present invention resides, briefly stated in a method of detecting oil pollutions on water surfaces, comprising the steps of providing echo signals obtained from optical radiation of a clean water area at two wavelengths; optically radiating an investigated water area at two wavelengths and obtaining echo signals from the optical radiation of the investigated water area at the two wavelengths; comparing the echo signals obtained from the radiation of the investigated area at two wavelengths with the echo signals obtained from the radiation of the clean water area; and based on the comparison, determining presence or absence of an oil pollution in the investigated water area.

Another feature of the present invention resides in a device for detecting oil pollution on water surfaces, comprising means for optically radiating an investigated water area at two wavelengths and obtaining echo signals from the optical radiation of the investigated water area at the two wavelengths; means for comparing the echo signals obtained from the radiation of the investigated area at two wavelengths with the echo signals obtained from the radiation of the clean water area; and means for determining presence or absence of an oil pollution in the investigated water area based on the comparison.

In accordance with a further feature of the present invention, the presence of oil pollution is determined when the following two inequalities are fulfilled simultaneously:

$$P(\lambda_1) > P_w(\lambda_1)\ P(\lambda_2) > P_w(\lambda_2)$$

$$N > 1$$

where:

$$N = \left(\frac{P(\lambda_1)}{P_w(\lambda_2)}\right) \Big/ \left(\frac{P(\lambda_2)}{P_w(\lambda_2)}\right)$$

$\lambda_1$, $\lambda_2$—wavelengths;
$P(\lambda_1)$, $P(\lambda_2)$ and $P_w(\lambda_1)$, $P_w(\lambda_2)$—powers of echo signals at the wavelengths $\lambda_1$, $\lambda_2$ received from investigated and clean water areas correspondingly.

The novel features of which are considered characteristic for the present invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
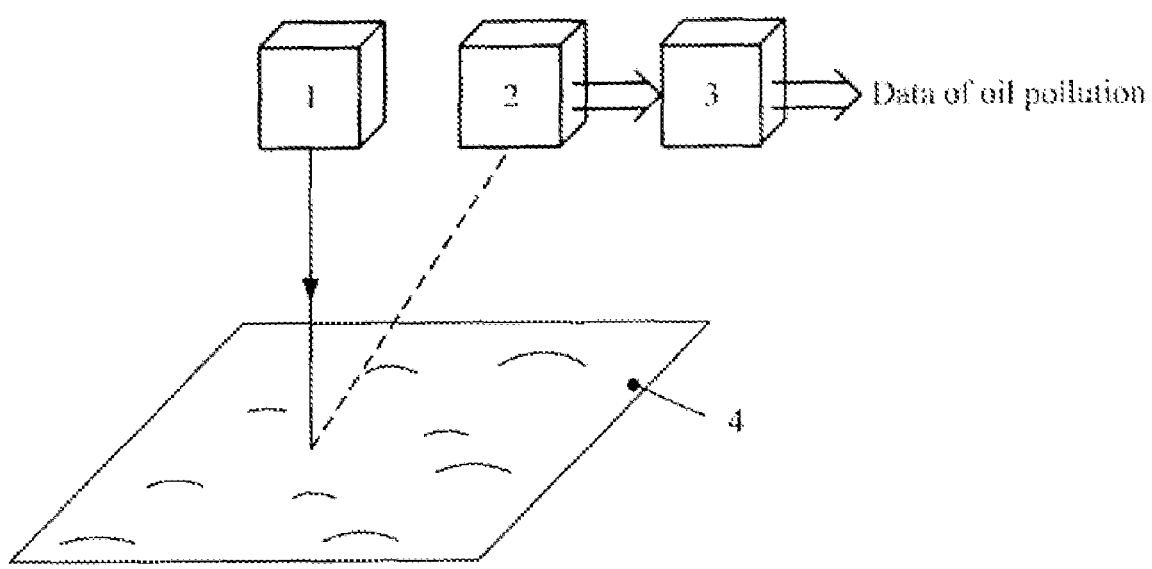
FIG. 1 of the drawings is a view schematically showing a method of and a device for detecting oil pollution on water surfaces, in accordance with the present invention.

A device for detecting oil pollution on water surfaces in accordance with the present invention includes a source of optical radiation 1 emitting optical radiation at two wavelengths, a photodetector 2 receiving radiation reflected from water surface at two wavelengths, a processing block 3, which calculates the relationship between power of echo signals reflected from investigated and clean water areas and checks the conditions corresponding to the inequalities as will be explained below. This allows detecting of oil pollution with high reliability.

The system operates in the following way.

The optical source 1 irradiates investigated water surface 4. For example the source can be placed on an aircraft The irradiation of the surface is conducted vertically downward at two wavelengths. Intensity of reflected radiation is received by the photodetector 2 at each wavelength. The signal from the photodetector 2 is supplied to the block 3, where the measured intensities reflected from the investigated area are compared with intensities reflected from clean water surface. The intensities from clean water area are received at the beginning of measurement during flight over known clean area and kept in memory of the block 3. The relationships of powers of echo signals reflected from investigated and clean water areas is calculated and the conditions corresponding to the inequalities are checked in the processing block. The conclusion about presence or absence of oil pollution is made. The presence of oil pollution is determined when the following inequalities are fulfilled simultaneously $$P(\lambda_1)>P_w(\lambda_1)\ P(\lambda_2)>P_w(\lambda_2)$$

$$N>1$$

where:

$$N = \left(\frac{P(\lambda_1)}{P_w(\lambda_1)}\right) \Big/ \left(\frac{P(\lambda_2)}{P_w(\lambda_2)}\right)$$

$\lambda_1, \lambda_2$—wavelengths;
$P(\lambda_1), P(\lambda_2)$ and $P_w(\lambda_1), P_w(\lambda_2)$—powers of echo signals at the wavelengths $\lambda_1, \lambda_2$ received from investigated and clean water areas correspondingly.

At flight over the investigated water area, the results of operation of the block are data arrays with information about presence of oil pollution.

Theoretical evaluation and experimental research show basic physics of remote detection of oil pollution on water surface using optical sensing brightness contrast of reflected radiation from clean water surface and from surface with oil film. The contrast is determined for two reasons: oil film has a different reflection coefficient as boundary "air-water" and oil pollution smooths sea roughness (see e.g. 1. Radiophysical Monitoring of Environment Pollution/M. L. Belov, V. A. Gorodnichev, V. I. Kozintsev et al-Moscow: Argus, 1994.-107 p; 2. Optic-electronic Systems of Ecological Monitoring Monitoring of Environment/V. I. Kozintsev, V. M. Orlov, M. L. Belov, et at-Moscow: Publ. House of BMSTU, 2002-528 p.) Control of only one of these effects decreases reliability of oil pollution detection. The area with smoothed roughness can be a window shadow after an island or high shore. The reflection coefficient can vary not only due to oil pollution but also due to the presence of foam or film of biological origin, etc.

For increase of reliability of oil pollution detection it is necessary to control two effects simultaneously—smoothing of wind roughness and changing of reflection coefficient of water surface. This is achieved using irradiation of water surface and reception of reflected signal at two wavelengths, calculating the powers of echo signal reflected from the investigated areas to powers of echo signal from clean water areas and examination of condition expressed in the above pre-sented inequalities.

The sounding wavelength $\lambda_1, \lambda_2$ must be selected in a special manner in order to fulfill the above inequality, There are many different variants of selection of pairs of wavelength $\lambda_1$ and $\lambda_2$. Calculation results of quantities $$\frac{P(\lambda_2)}{P_w(\lambda_2)}$$

and N are given for example in the Table at three pairs of wavelength 2.5 and 1.06 µm; 5.9 and 2.86 µm; 11 and 1.43 µm. The calculations were obtained in the cases of different types of investigated water surface: oil pollution, area with smoothed wind roughness, area with foam, clean water surface. It can be seen from Table 1 that the conditions in accordance with the equalities are fulfilled at all three pairs of the wavelengths. This allows distinguishing oil pollution from areas with smoothed wind roughness and areas with foam to make a decision about presence of oil pollution with high reliability

TABLE 1

| Nature of investigated area of water surface | 5.9 and 2.86 µm | | 11 and 1.43 µm | | 2.5 and 1.06 µm | |
| --- | --- | --- | --- | --- | --- | --- |
| | N | $\frac{P(\lambda_2)}{P_w(\lambda_2)}$ | N | $\frac{P(\lambda_2)}{P_w(\lambda_2)}$ | N | $\frac{P(\lambda_2)}{P_w(\lambda_2)}$ |
| Areas with oil pollution | 1.34 | 6.74 | 2.1 | 6.71 | 1.42 | 6.71 |
| Areas with smoothed wind roughness | 1 | 10 | 1 | 10 | 1 | 10 |
| Areas with foam | 1 | 1 | 0.085 | 11.8 | 0.23 | 28 |
| Clean water area | 1 | 1 | 1 | 1 | 1 | 1 |

While the known methods of oil pollution detection on water surface can erroneously identify areas with smoothed wind roughness and areas with foam as "oil pollution", the two-wavelength remote method of oil pollution detection on water surface of the present invention provides detection of oil pollution on water surface with high reliability, because the method distinguishes areas with oil pollution from areas with smoothed wind roughness and areas with foam.

it will be understood that each of the elements described above, or two or more together, may also find a useful application in other types of constructions differing from the type described above.

While the invention has been illustrated and described as embodied in a method of and a device for detecting oil pollution on water surfaces, it is not intended to be limited to the details shown, since various modifications and structural changes may be made without departing in any way from the spirit of the present invention.

Without further analysis, the foregoing will so fully reveal the gist of the present invention that others can, be applying current knowledge, readily adapt it for various applications without omitting features that, from the standpoint of prior art, fairly constitute essential characteristics of the generic or specific aspects of this invention.

We claim:

1. A method of detecting oil pollutions on water surfaces from an aircraft that takes into consideration smoothing of wind roughness and changing reflection coefficients on water surfaces, comprising the steps of: optically radiating a known clean water area at two wavelengths; optically radiating an investigated water area at two wavelengths; obtaining echo signals from the optically radiated known clean water area at two wavelengths and the investigated water area at two wavelengths; comparing the echo signals obtained from the radiation of the investigated water area at the two wavelengths with the echo signals obtained from the radiation of the clean water area at the two wavelengths, wherein comparing the echo signals includes comparing the powers of the echo signals obtained from the radiated investigated water area and the radiated known clean water area; and determining the presence of oil pollution on a water surface based on the following two inequalities fulfilled simultaneously:

$$P(\lambda_1)>P_w(\lambda_1), P(\lambda_2)>P_w(\lambda_2)$$

and N>1 where:

$$N = \left(\frac{P(\lambda_1)}{P_w(\lambda_1)}\right) \Big/ \left(\frac{P(\lambda_2)}{P_w(\lambda_2)}\right)$$

$\lambda_1$, $\lambda_2$ are wavelengths; and $P(\lambda_1)$, $P(\lambda_2)$ and $P_w(\lambda_1)$, $P_w(\lambda_2)$ are powers of echo signals at the wavelengths $\lambda_1$, $\lambda_2$ received from investigated and clean water areas respectively.

2. The method of claim 1, wherein during the flight of the aircraft, the known clean water area is optically radiated at two wavelengths before the investigated area is optically radiated at two wavelengths.

3. The method of claim 1, wherein the known clean water area and the investigated area are optically radiated in a vertically downward direction from the aircraft.

4. A device for detecting oil pollutions on water surfaces from an aircraft that takes into consideration smoothing of wind roughness and changing reflection coefficients on water surfaces, comprising: means for optically radiating a known clean water area at two wavelengths; means for optically radiating an investigated water area at two wavelengths; means for obtaining echo signals from the optically radiated known clean water area at two wavelengths and the investigated water area at two wavelengths; processing block means programmed for comparing the echo signals obtained from the radiation of the investigated water area at two wavelengths with the echo signals obtained from the radiation of the clean water area at two wavelengths, wherein the powers of the echo signals obtained from the radiated investigated water area and the radiated known clean water area are compared; and the presence of oil pollution detected on a water surface is based on processing block means calculating the following inequalities fulfilled simultaneously:

$$P(\lambda_1) > P_w(\lambda_1), P(\lambda_2) > P_w(\lambda_2)$$

and $N > 1$
where:

$$N = \left(\frac{P(\lambda_1)}{P_w(\lambda_1)}\right) \Big/ \left(\frac{P(\lambda_2)}{P_w(\lambda_2)}\right)$$

$\lambda_1$, $\lambda_2$ are wavelengths; and $P(\lambda_1)$, $P(\lambda_2)$ and $P_w(\lambda_1)$, $P_w(\lambda_2)$ are powers of echo signals at the wavelengths $\lambda_1$, $\lambda_2$ received from investigated and clean water areas respectively.

* * * * *